United States Patent [19]

Busta et al.

[11] 4,198,261
[45] Apr. 15, 1980

[54] METHOD FOR END POINT DETECTION DURING PLASMA ETCHING

[75] Inventors: Heinz H. Busta, Park Ridge; Robert E. Lajos, Crystal Lake; Kul B. Bhasin, Schaumburg, all of Ill.

[73] Assignee: Gould Inc., Rolling Meadows, Ill.

[21] Appl. No.: 857,384

[22] Filed: Dec. 5, 1977

[51] Int. Cl.² ........................................... H01L 21/306
[52] U.S. Cl. ..................................... 156/626; 156/643; 156/655; 356/364; 356/368; 356/381; 356/382
[58] Field of Search ............... 156/626, 643, 646, 345, 156/662, 655; 356/108, 114, 118, 364, 368, 381, 382

[56] References Cited

U.S. PATENT DOCUMENTS

| | | | |
|---|---|---|---|
| 3,612,692 | 10/1971 | Kruppa | 356/108 |
| 3,953,265 | 4/1976 | Hood | 156/626 |
| 3,985,447 | 10/1976 | Aspnes | 356/118 |
| 3,992,104 | 11/1976 | Watanabe | 356/368 |
| 4,035,082 | 7/1977 | Kirschen | 356/364 |
| 4,039,370 | 8/1977 | Kleinknecht | 156/626 |
| 4,068,016 | 1/1978 | Wilmanns | 427/10 |
| 4,141,780 | 2/1979 | Kleinknecht | 156/662 |

OTHER PUBLICATIONS

Gottesfeld et al, "The Monitoring . . . Ellipometes" Surface Science, vol. 44, No. 2 (Aug.1974), pp. 377–388.
Rode et al, "Crystal Etch . . . Interferometry" The Review of Scientific Instruments, vol. 41, No. 5 (May 1970), pp. 672–675.
Herring et al, "Multiple . . . System" IBM Technical Disclosure Bulletin., vol. 17. No. 7 (Dec. 1874), pp. 1946–1947.
Moritz, "Continuous . . . Layers" IBM Technical Disclosure Bulletin, vol. 19 No. 7 (Dec. 76). pp. 2579–2580.

Primary Examiner—Jerome W. Massie
Attorney, Agent, or Firm—Phillip H. Mayer; Charles E. Snee, III

[57] ABSTRACT

A method and apparatus for detecting the end point of a plasma etching process comprising the use of an optical technique in which light is beamed on the layer to be etched and the resulting beam that is reflected and refracted is detected. Sharply different values of light intensity can be detected when the desired layer is etched and the next layer receives the light beam. A laser is preferably used to obtain an intense and substantially uniform frequency light source.

1 Claim, 7 Drawing Figures

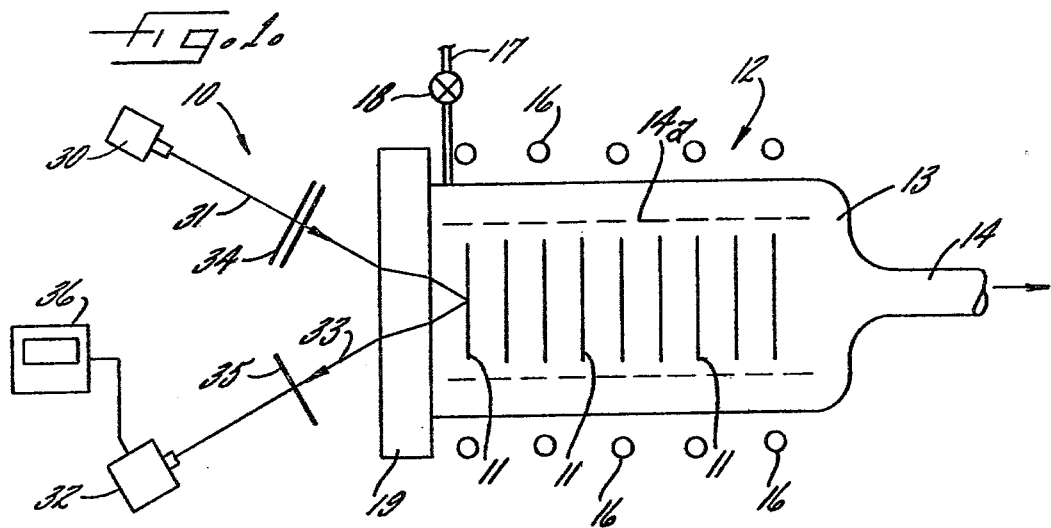
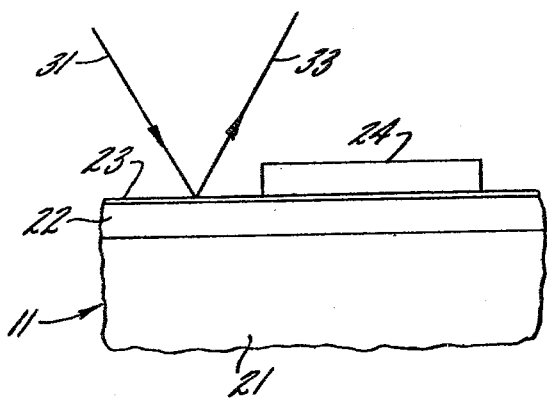
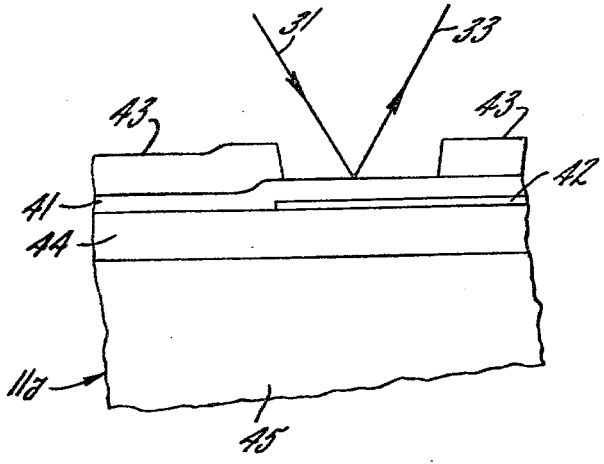
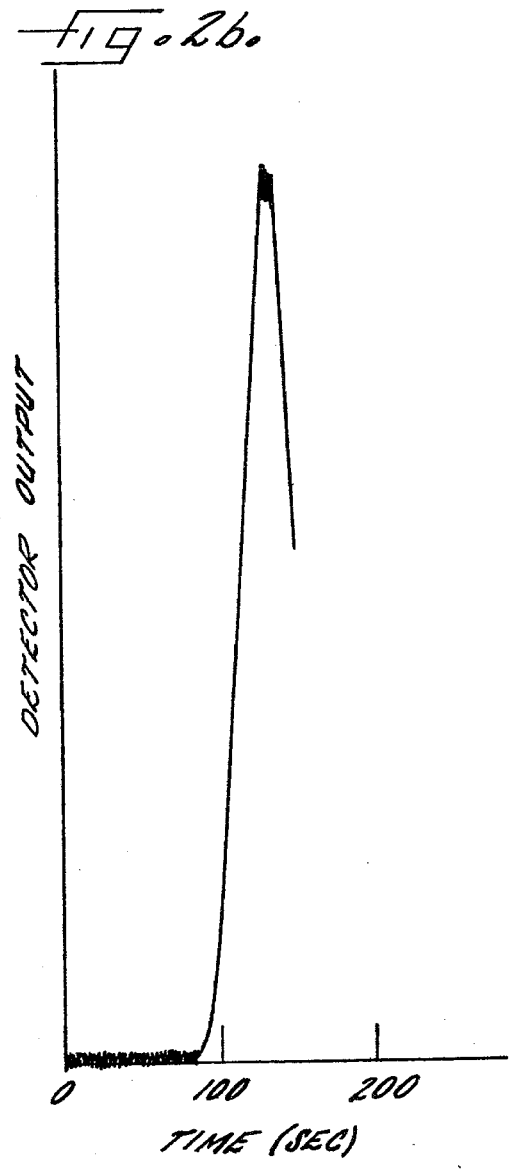

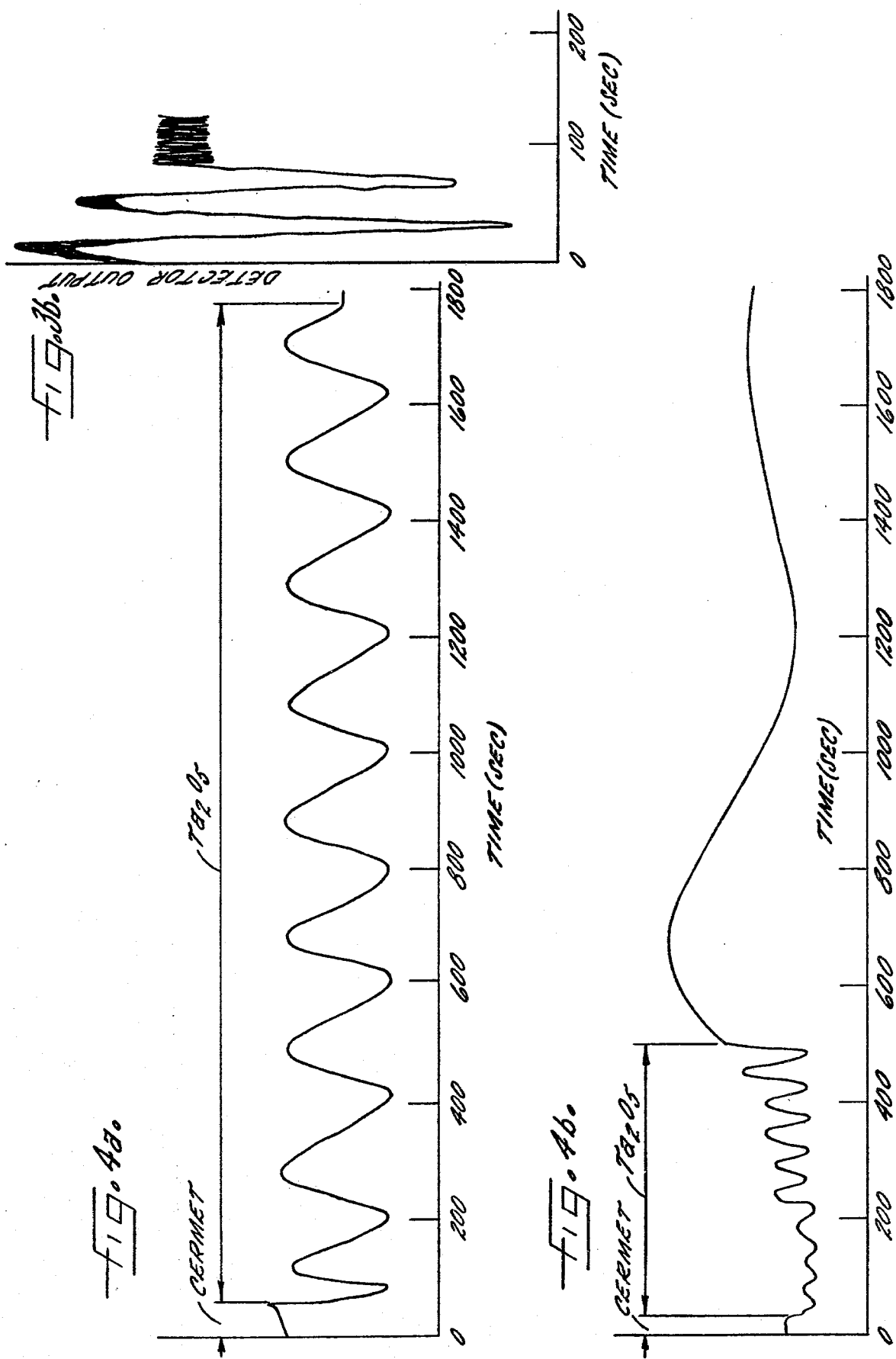

METHOD FOR END POINT DETECTION DURING PLASMA ETCHING

The present invention relates generally to plasma etching, as practiced in the manufacture of solid state electronic devices, and more particularly concerns detecting desired end points during such etching.

Within the last five or six years, the technique of plasma etching has gained popularity for the manufacture of semi-conductors, integrated circuits, and similar electronic devices. Plasma etching is the selective removal of material by reaction with chemically active gases created by an RF power induced glow discharge environment in the etching chamber. As compared with wet chemical etching, it is dry, cleaner, more economical, free of volumes of waste to be disposed of and, properly controlled, capable of sharper etching with less undercutting.

Plasma etching is controlled by a number of parameters including the nature of the etching gas, the RF power level used, the gas flow rate and chamber pressure, the temperature, and the load or volume of material to be etched. Because of the many variables, empirically setting process specifications and obtaining run-to-run reproducibility has been very difficult.

Plasma etching chambers typically have viewing windows of optical quartz. Skilled, experienced operators are sometimes able to detect a color intensity change of the plasma during the desired etching process as the products generated by the etching often change when etching is complete—indicating that an end point has been reached and exceeded. However, this kind of control is highly subjective and rather gross.

Another very subjective control for an experienced operator is the visual detection of the color change in a non-absorbing film as it is etched away or, similarly, noting the disappearance of a metallic film.

Some commercial etchers utilize the color or intensity change phenomenum referred to above to achieve more automatic detection of etching end point through utilizing a monochrometer or an optical filter allowing the instrument to "see" and signal the desired color or intensity change. This control tenchique has been mainly used for controlling the stripping of photoresist from a batch of devices where a relatively large volume of material is involved.

Another etching control disclosed in the literature and utilized commercially involves directing the gases exhausted from the etching chamber through a mass spectrometer. Again, the desired etching produces a gas component that is detected by the spectrometer and, when that gas trace changes, the etching end point has been reached. Not only is this type of instrumentation quite expensive, but it also requires a reasonable volume of material for an etching step to produce enough distinctive material to be traced.

Turning briefly from plasma etching, the measurement of thin transparent film thickness has long been accomplished using an ellipsometer. Such instruments are generally disclosed in U.S. Pat. Nos. 3,874,797 and 3,824,017, for example. An ellipsometer utilizes a light source of narrow band width to reflect a light beam from the sample under investigation to a light detector. Rotatable polarizing filters are positioned in both the source and the reflected light paths. The thickness and refractive index of the film sample are related to the angle of light beam incidence and relative angular positions of the polarizing filters required to block light from the detector, and, typically, nomographs or small computer programs associate settings of the ellipsometer with thickness and properties of the film sample. Commercial ellipsometers utilize laser light sources to develop a fixed frequency beam which is highly collimated to permit study of small samples.

It is the primary aim of the invention to utilize certain aspects of optical measurement for the direct detection of end point during plasma etching.

More particularly, it is an object of the invention to provide a method and apparatus for detecting the completed plasma etching of a given area, so that the plasma etching step can be controlled no matter how the etching variables, including the etching load, are modified or changed.

Another object is to provide a method and apparatus as characterized above that greatly facilitates plasma etching process engineering by permitting determination of absolute and relative etching rates, and thickness of dielectric layers, utilizing single prototype devices.

Other objects and advantages of the invention will become apparent upon reading the following detailed description and upon reference to the drawings, in which:

FIG. 1 is a schematic diagram of an apparatus embodying the invention;

FIG. 2A is a fragmentary diagrammatic section showing a typical etching operation;

FIG. 2B shows a representative detector output for the etching operation of FIG. 2A;

FIG. 3A shows a second typical type of etching operation;

FIG. 3B shows a representative detector output for the etching operation of FIG. 3A; and FIGS. 4A and 4B show detector outputs reflecting differences in the etching operation.

While the invention will be described in connection with a preferred embodiment and procedure, it will be understood that we do not intend to limit the invention to those embodiments. On the contrary, we intend to cover all alternatives, modifications and equivalents as may be included within the spirt and scope of the invention as defined by the appended claims.

Turning now to the drawings, there is shown in FIG. 1 a diagram of an apparatus 10 for detecting the end point when etching layers from solid state devices 11 in a plasma etching apparatus 12. As is conventional, the apparatus 12 includes a vessel 13 evacuated through a neck portion 14 which contains an RF tunnel 14a in which the devices 11 are mounted. The apparatus 12 also includes RF coils 16 surrounding the vessel 13 for creating a glow discharge, plasma effect within the vessel utilizing gas introduced through a line 17 at a rate controlled by a valve 18.

For giving access to the interior of the vessel 13 and also allowing an operator to observe the process, there is a removable optical quartz window 19 sealed across an open end of the vessel 13.

A typical solid state device 11 intended for etching is shown diagrammatically in FIG. 2A with the layer thicknesses being highly exaggerated. The device 11 includes a substrate 21 covered with a layer of dielectric insulator 22 which in turn is covered with a layer of conductive material 23 like a cermet or metal. The process step assumed is to etch away the conductive layer 23 except for those portions underlying applied areas of a photoresist 24 but not, of course, to remove the underlying dielectric 22.

In carrying out the invention, the device 11, together with similarly formed devices intended for the same process if multiple processing is desired, is supported in the vessel 13 with one device positioned adjacent the window 19 so that the layer 23 to be etched can be "seen". The apparatus 10, in accordance with the invention, includes a light source 30 for obliquely directing a beam of substantially uniform frequency light 31 onto the layer 23 to be etched, a light detector 32 positioned for sensing reflected and refracted light 33 from the layer 23, a pair of rotatable polarizing filters 34 and 35 in both the projected beam 31 and the reflected beam 33, and a quarter wave plate 34a in the projected beam. Since in this instance a non-transparent layer 23 is being etched, the filters 34, 35 are rotated so that initially no light reaches the detector 32. However, when the layer 23 is etched away exposing the underlying transparent dielectric 22, the oblique light beam 31 is both reflected and refracted back, with the result that light beam 33 is passed to the detector 32 causing a sharp, clear reading. That reading obviously signals the end point of the particular etching process.

Preferably, the light source 30 is a laser so that the resulting highly collimated light beam of uniform frequency can be focused on very small areas to be etched. The area so "looked" at serves as the control sample for all etching of all devices 11 in a single step.

If the filters 34, 35 are not used, there will still be clear and sharp differences in the light intensity reaching the detector 32 when a layer has been etched away and a completely different layer reached. Thus, the method can be so practiced, although not using the polarizing filters does not permit setting a no light, null condition that is better suited for automatic control.

As a feature of the invention, the output of the detector 32 is coupled to a strip chart recorder 36 so that the output can be plotted against time. In the example so far discussed, FIG. 2B is a typical chart record where, after approximately 100 seconds the conductive layer 23 has been etched away and a formerly zero output increases sharply.

Another example will suggest the utility of the strip chart recorder 36. A solid state device 11a (see FIG. 3A) is assumed to be ready for an etching step to establish an electrical connection point through a dielectric passivation layer 41 to a conductive layer 42 in a region defined and surrounded by layers of photoresist 43. The conductive layer 42, again typically of metal or cermet, is on an insulated layer 44 that in turn is on a substrate 45.

In this case, the resulting strip chart record, FIG. 3B, first shows the maximum and minimum output wave form characteristic of photometric measurement of the thickness of a transparent layer, which is the dielectric passivation layer 41, and, when etching is completed, the end point would be signalled by a substantially fixed, nonrefracted, reflected light output being detected. In the illustrated chart FIG. 3B, this occurs at about 100 seconds. As will be appreciated by those skilled in the art, the wave frequency pictured at the left of the chart FIG. 3B as the dielectric is etched is related to the wave length of the light generated by the source 30, the index of refraction of the film 41, the angle of incidence of the light source, and the complex index of refraction of the underlying layer 42. Thus, not only will the chart record show how long it took to reach etching end point, but will also show how thick the layer was that was etched, i.e., the etching rate is determined.

Film thickness is shown by the spacing of the successive minima of the curve, which spacing is $\alpha\tau/2n \rightarrow \tau$ being the wave length of the monochromatic light, n being the index of refraction of the film, and $\alpha$ being a prefactor depending upon light wave length, film refraction, angle of incidence, and refraction from the underlying layer.

This last capability has great utility in process engineering plasma etching steps. FIGS. 4A and 4B are strip chart records showing the etching, during successive etching procedures, of the same successive layers of, first, a cermet layer and, second, a layer of tantalum oxide with the only difference between the etching processes being a change in one of the many plasma etching variables. In this case, a change was made in the composition of the etching gas with the result that the process engineer can readily see from the records that such a change in that gas composition slightly increased the cermet etching rate but greatly increased the tantalum oxide etching rate. This kind of precise information allows a process engineer to optimize production of given solid state devices both by optimizing etching rates and also assuring that the plasma etching parameters for a given etching step are such that there is a significant etching rate difference when end point is reached, thereby assuring proper detection and minimizing the likelihood of undercutting on the one hand or incomplete etching on the other.

It will be apparent that the output of the detector 32 could be also coupled to a control circuit for automating the cutoff of the etching process when the the appropriate signal is senses.

Those familiar with the art will now appreciate that a method and apparatus has been disclosed giving good reliable control for determining the end point of a plasma etching operation even though very small areas are involved. The technique also permits the obtaining of valuable information for proper, and most reliable, plasma etching conditions.

We claim as our invention:

1. A method of detecting the end point of etching a first layer of material from a second layer of material wherein said materials have different indices of refraction, comprising the steps of:

mounting said materials in an etching chamber;

projecting a beam of light toward a portion of the material to be etched via a first polarizing filter;

reflecting said beam of light from said portion of the material to be etched;

following reflection, passing said beam of light toward a detector, via a second polarizing filter;

adjusting said first and second filters relative to said beam of light so that essentially no light will reach the detector following reflection and/or refraction from either said first or said second layer of material; and detecting an abrupt change in the intensity of light reaching the detector due to the change in index of refraction from the first layer to the second, as an indication of said end point of etching.

* * * * *